(12) United States Patent
Bordier et al.

(10) Patent No.: US 8,119,855 B2
(45) Date of Patent: Feb. 21, 2012

(54) RESISTANCE TO ABIOTIC STRESS IN PLANTS

(75) Inventors: Adeline Amandine Colette Bordier, Saint Pol de Leon (FR); Dianne Antoinette Maria Van Der Kop, Wageningen (NL); Anne Douwe De Boer, Dreumel (NL); Paul Alexandre Passarinho, Heerewaarden (NL)

(73) Assignee: Expressive Research B.V., Wageningen (NL)

( * ) Notice: Subject to any disclaimer, the term of this patent is extended or adjusted under 35 U.S.C. 154(b) by 0 days.

(21) Appl. No.: 12/630,012

(22) Filed: Dec. 3, 2009

(65) Prior Publication Data

US 2010/0146664 A1 Jun. 10, 2010

Related U.S. Application Data

(63) Continuation of application No. PCT/NL2008/050350, filed on Jun. 4, 2008.

(30) Foreign Application Priority Data

Jun. 5, 2007 (EP) .................................... 07109621

(51) Int. Cl.
A01H 1/00 (2006.01)
A01H 5/00 (2006.01)
C12N 5/04 (2006.01)
C12N 15/82 (2006.01)

(52) U.S. Cl. ........ 800/278; 800/289; 800/298; 435/410; 435/419; 435/468

(58) Field of Classification Search ........................ None
See application file for complete search history.

(56) References Cited

U.S. PATENT DOCUMENTS 6,063,731 A * 5/2000 Back et al. .................... 504/138
2009/0138991 A1* 5/2009 Reuzeau ....................... 800/287

FOREIGN PATENT DOCUMENTS

WO 01/45492 A2 6/2001
WO 2006/011788 A1 2/2006

OTHER PUBLICATIONS

Zhang et al., J Mol Evol (2006), 63:612-621.*
Krishna, J Plant Growth Regul (2003) 23:289-297.*
International Search Report relating to corresponding PCT/NL2008/050350.

* cited by examiner

*Primary Examiner* — Eileen B O Hara
(74) *Attorney, Agent, or Firm* — Banner & Witcoff, Ltd.

(57) ABSTRACT

The invention relates to a method for conferring tolerance to abiotic stress to plants or plant cells. This is done by introducing a gene coding for an RKS protein, especially a gene coding for an RKS subgroup II protein, more specifically RKS1, RKS4 or truncated RKS4, or a gene from RKS subgroup III, more preferably RKS12. The effect of overexpression of the RKS gene may be enhanced by additionally treating the plant with a brassinosteroid compound.

13 Claims, 5 Drawing Sheets

RESISTANCE TO ABIOTIC STRESS IN PLANTS

RELATED APPLICATIONS

This application is a continuation of PCT application number PCT/NL2008/050350 designating the United States and filed Jun. 4, 2008; which claims the benefit of European patent application number EP 07109621.8 filed Jun. 5, 2007; both of which are hereby incorporated herein by reference in their entireties.

FIELD OF THE INVENTION

The invention relates to the field of plant genetics, especially to the field of genetically engineering plants to increase their tolerance to abiotic stress.

BACKGROUND

Plants are highly flexible organisms, forced to efficiently and quickly adapt to (changes in) their environment. Unable to move, they have evolved morphological and physiological strategies that allow growth even in challenging environments. However, environmental adaptation is not always in harmony with optimal economic traits desired by the farmer or the consumer. Plants, which are fully adapted to a specific environment often have relatively low yields or nutritional value or lack ornamental characteristics. Conversely, heavily bred varieties designed to fit the needs of farmers and consumers, are often affected by environmental circumstances and/or changes.

Abiotic stress or environmental stress is stress caused to plants in other ways than through living organisms. Examples of abiotic stress are environmental conditions such as: high salinity, osmotic stress, oxidative stress, (extreme) heat and (extreme) cold and drought. Crop losses and crop yield losses of major crops such as rice, maize (corn) and wheat caused by these stresses represent a significant economic and political factor and contribute to food shortages in many developing countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. Similar alterations can be observed by prolonged exposure to extreme heat or cold. These great changes in metabolism ultimately lead to cell death and consequently yield losses.

In 1979 a novel plant growth-promoting factor, termed brassinolide, was isolated from the pollen of rape (*Brassica napus*) and identified as a novel type of steroid lactone. It was found that brassinolide-like steroid compounds (called brassinosteroids) occur in all plant species examined at very low concentrations and had a function in adapting the plants to combat both biotic and abiotic stress (for review, see Mandava, Ann. Rev. Plant Physiol. Plant Mol. Biol. 39 (1988), 23-52). Initial studies of the physiological action of brassinolide showed that this particular factor (i) accelerated the germination and growth of plant seedlings at low temperatures, (ii) promoted the increase of cell size and elongation by induction of a longitudinal arrangement of cortical microtubuli and cellulose microfilaments on the surface of cells, (iii) promoted xylem differentiation by amplifying the tracheal elements, (iv) resulted in significant increase of dry weight of plants and their fruits, (v) promoted leaf unrolling and enlargement, (vi) induced H+ export and membrane hyperpolarization characteristic for auxin induced cell growth, (vii) inhibited the division of crown-gall tumour cells and radial growth of stems, (viii) repressed anthocyanin production in light-grown plants, (ix) inhibited the de-etiolation induced, e.g. by cytokinin in the dark, (x) promoted tissue senescence in the dark, but prolonged the life-span of plants in the light and (xi) induced plant pathogen resistance responses to numerous bacterial and fungal species (listed by Mandava (1988), loc. cit.). Recent work has further confirmed the protective role of brassinosteroids against a wide range of abiotic stresses (drought, cold and salt, Kagale et al., Planta 225 (2007), 353-364).

Following the initial isolation of and physiological studies with brassinolides, numerous brassinosteroid compounds, representing putative biosynthetic intermediates, were identified in different plant species. Because the in vivo concentration of these compounds was found to be extremely low, efforts had been made to develop methods for chemical synthesis of these compounds (for review, see: Adam and Marquardt, Phytochem. 25 (1986), 1787-1799). These compounds were tested in field experiments using soybean, maize, rice and other crops as well as trees in order to confirm the results of physiological studies. However, the field trials showed that due to poor uptake of steroids through the plant epidermis, the amount of steroids required for spraying or fertilization was considerable, thereby making the use of brassinosteroids for providing plants with resistance to (a)biotic stress practically impossible.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, heat/cold, salt and other tolerances in model tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

Expression and function of abiotic stress-inducible genes have been well studied at a molecular level. Complex mechanisms seem to be involved in gene expression and signal transduction in response to the stress. These include the sensing mechanisms of abiotic stress, modulation of the stress signals to cellular signals, translocation to the nucleus, second messengers involved in the stress signal transduction, transcriptional control of stress-inducible genes and the function and cooperation of stress-inducible genes.

In animal cells, phosphatidylinositol-specific phospholipase C (PI-PLC) plays a key role in early stages of various signal-transduction pathways. Extracellular stimuli such as hormones and growth factors activate PI-PLCs. PI-PLC hydrolyzes phosphatidylinositol 4,5-biphosptate (PIP2) and generates two second messengers, inositol, 4,5-triphosphtate (IP3) and 1,2-diacylglycerol (DG). IP3 induces the release of intracellular Ca<2+> into the cytoplasm, which in turn causes various responses therein. DG and PIP2 also function as second messengers and control various cellular responses.

In plants, similar systems are thought to function in abiotic stress response. It is clearly demonstrated that phospholipases A, C or D (PLA, PLC or PLD), depending upon their site of cleavage, play a role in the early signal transduction events that promote the cell volume changes associated with osmotic stress and osmoregulation in plants which is important for plant stress tolerance (Wang X. et at., 2000, Biochemical Society Transactions. 28; 813-816; Chapman K D, 1998 Tr. Plant Sci. 3:419-426). For example, in guard cells, abscisic acid (ABA)-induced stomatal closure is mediated by rapid activation of PIP2-PLC. This leads to an increase in IP3 levels, a rise in cytosolic calcium, and the subsequent inhibition of K+ channels. For example, a gene for phospholipase C, AtPLC was demonstrated to be rapidly induced by drought and salt stresses in *Arabidopsis thaliana* (Hirayama, T. et al., 1995 Proc. Natl. Acad. Sci. 92:3903-3907).

As mentioned above, $Ca^{2+}$ ions play important roles as second messengers in various signal-transduction pathways in plants. Marked increase in intracellular $Ca^{2+}$ concentration has been observed upon stimulation by wind, touch, abiotic stresses (cold, drought and salinity) or fungal elicitors. Several genes for $Ca^{2+}$ binding proteins with a conserved EF-hand domain have been isolated and showed increased expression level upon abiotic stress treatment (Frandsen G. et al., 1996 J. Biol. Chem. 271:343-348; Takahashi S. et al., 2000 Pant Cell Physiol. 41:898-903).

The enigmatically named 14-3-3 proteins have been also the subject of considerable attention in recent years since they have been implicated in the regulation of diverse physiological processes in eukaryotes ranging from slime moulds to higher plants. In plants, many biological roles for 14-3-3 proteins have been suggested. The most significant of these include roles in the import of nuclear encoded chloroplast proteins, in the assembly of transcription factor complexes and in the regulation of enzyme activity in response to intracellular signal transduction cascades (Chung H J. et al., 1999 Tr. Plant Sci. 4:367-371). The native 14-3-3 proteins are homo- or heterodimers and, as each monomer has a binding site, a dimer can potentially bind two targets, promoting their association. Alternatively, target proteins may have more than one 14-3-3-binding site.

Several functions have been proposed for the 14-3-3 proteins in terms of involvement of plant stress tolerance. The 14-3-3 proteins could function as regulators in stress signal transduction. For example, RCI14A and RCI14B genes are induced by cold treatment in *Arabidopsis* and are highly homologous to the 14-3-3 proteins. The rise in the RCI transcript levels observed in response to cold treatment suggests a role for the RCI proteins in the stress signalling transduction pathway (Jarillo J A et al., 1994 Plant Mol. Biol. 25:693-704)

Due to the commercial consequences of environmental damage to crops, there is an interest in understanding the stress response signal transduction mechanisms in plants and how these can be manipulated to improve a plant's response to environmental damage. There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

The invention comprises a method to confer abiotic stress tolerance to a plant by providing said plant with a nucleotide sequence encoding an RKS gene. Possibly said RKS gene is a truncated RKS gene, encoding the extracellular domain of the receptor. The RKS gene is preferably chosen from the group consisting of RKS subgroup II (RKS1, RKS4, RKS5, RKS7, RKS11, and RKS14), more specifically RKS1 or RKS4 and truncated RKS4 or from the group consisting of RKS subgroup III (RKS0, RKS8, RKS10, RKS12 and RKS13), more specifically RKS12.

Further preferred is a method wherein the plant is additionally treated with a brassinosteroid, wherein said brassinosteroid is preferably selected from the group consisting of brassinolide, epibrassinolide, homobrassinolide and analogs.

Also part of the invention is the use of an RKS gene, more specifically a gene from RKS subgroup II, more preferably RKS1 or RKS4 or truncated RKS4 or from the group consisting of RKS subgroup III (RKS0, RKS8, RKS10, RKS12 and RKS13), more specifically RKS12 for conferring tolerance to abiotic stress to a plant or plant cell.

Germination frequencies were scored during 14 or 17 days after stratification (A and C, respectively) and are shown as percentages that correspond to the average of 3 to 5 replicates, each made of ca. 100 seeds. Error bars represent the standard error.

A. Germination of RKS4 overexpression lines on medium supplemented with 180 mM NaCl. Four RKS4 overexpression lines (p35S::RKS4; RKS4-OX1 to OX4) are represented together with their wild-type (Ws-0).

B. Correlation between the expression level of the RKS4 gene and the ability to germinate under high salinity conditions. The expression level of the RKS4 gene was determined by quantitative RT-PCR in the overexpression lines RKS4-OX1 to OX4 and is represented as fold-change as compared to the wild-type (WT) expression level. It was plotted against the germination frequency of the corresponding lines at 14 days after stratification (see panel A). Linear regression coefficient ($R^2$=0.972) and corresponding equation are shown on the chart.

C. Germination of RKS1, RKS12 and RKS14 overexpression lines on medium Supplemented with 200 mM NaCl. The right panel shows the germination frequencies obtained for lines in the Ws-0 ecotype whereas those obtained in the Col-0 ecotype are shown in the left panel.

Figure 2:
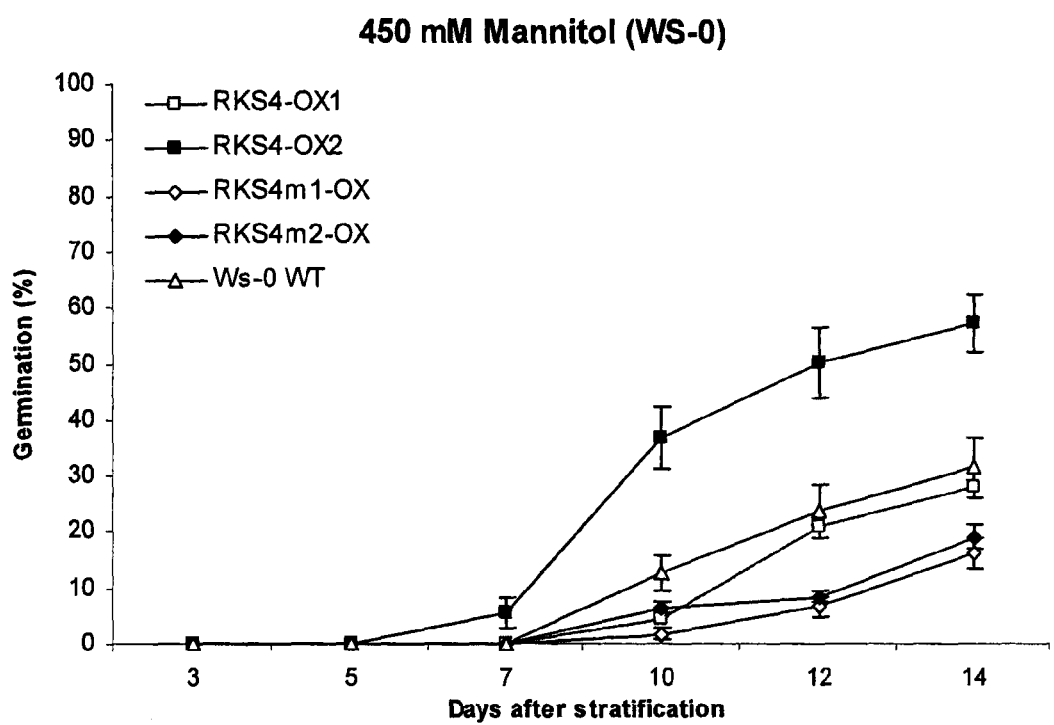

FIG. 2. Effect of osmotic stress on *Arabidopsis* seed germination.

Germination of RKS4 overexpression lines on medium supplemented with 450 mM mannitol was scored during 14 days after stratification and is shown as percentage corresponding to the average of 3 to 5 replicates, each made of ca. 100 seeds. Error bars represent the standard error. Four RKS4 overexpression lines (p35S::RKS4; RKS4-OX1 to OX4) are represented together with their wild-type (Ws-0). RKS4-OX1 to OX4: p35S::RKS4; RKS4m1-OX: p35S::RKS4Δ531; RKS4m2-OX: p355::RKS4Δ618; Ws-0 WT: wild-type.

FIG. 3. Effect of frost damage on *Arabidopsis* growth (rosette size)

A. Rosette size of transgenic lines expressing truncated forms of the RKS4 gene in the Col-0 ecotype (left panel) or in the Ws-0 ecotype (right panel). Rosette diameters were measured right after treatment (0 days) and 14 days later. Treatment was applied in the dark for 1 h at −25° C. (−25) or at room-temperature (Ctrl). Each bar corresponds to the average in mm of 20 individual measurements and the error bars show the standard error. The letters above the bars indicate groups of significance. No significant difference was found between samples with the same letter, whereas each letter corresponds to a group that is significantly different from all others. Differences between treated and non-treated plates are also materialised by the dashed arrows. Col-0: wild-type of rks4-1: T-DNA insertion line rks4-1; Ws-0: wild-type of RKS4m1-OX: p35S::RKS4Δ531 and RKS4m2-OX: p35S::RKS4Δ618.

B. Relative growth after frost damage. The effect of frost damage on plant growth is represented by differences in growth rate between treated and non-treated plant (−25 C vs. Ctrl=rosette diameter at day 14 (−25 C)/rosette diameter at day 14 (Ctrl)). Relative growth is also expressed in relation to the corresponding wild-type (vs WT=relative growth (−25 C vs. Ctrl) of the transgenic line/relative growth (−25 C vs. Ctrl) of the wild-type. Col-0 WT: wild-type of rks4-1: T-DNA insertion line rks4-1; Ws-0 WT: wild-type of RKS4m1-OX: p35S:: RKS4Δ531 and RKS4m2-OX: p35S::RKS4Δ618.

Figure 4:
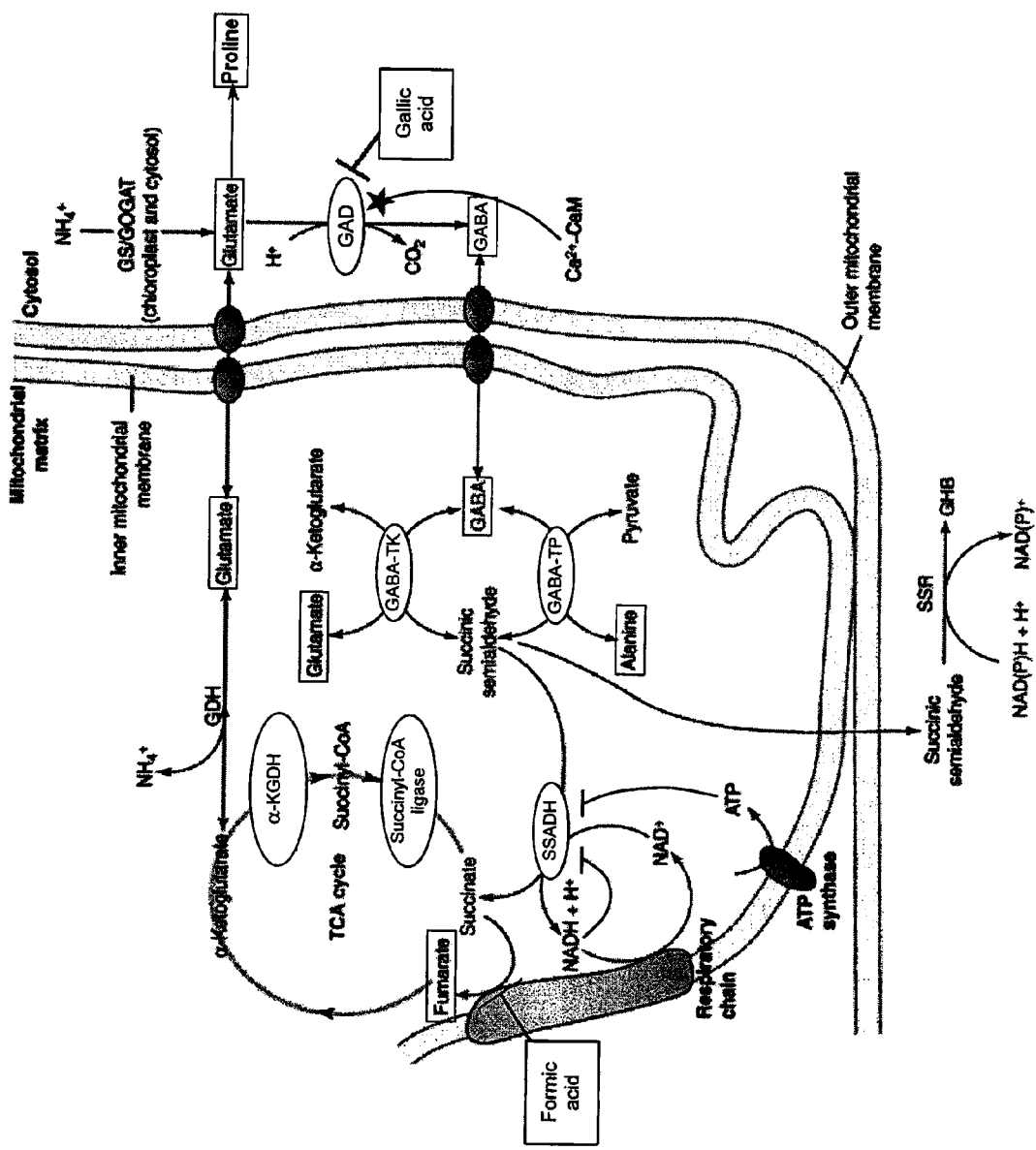

FIG. 4. Schematic view of the GABA shunt metabolic pathway (adapted from Bouché and Fromm (2004) TIPS 9: 110-115). Boxed compounds are more abundant in RKS4 transgenic plants, whereas shaded compounds are less abundant as compared to the wild-type.

DETAILED DESCRIPTION

Abiotic stress can take many forms and can have many effects. In Table 1 a short overview of the main forms of abiotic stress, how to achieve these in experiments and the effects on plants is given. As can be seen, nearly all abiotic stress forms result in an impaired plant growth, which thus appears to be the dominating effect.

TABLE 1

| Stress | Corresponding treatment | Effect on the plant |
| --- | --- | --- |
| Salt | Growth on NaCl (in vitro) | Deregulation of ion homeostasis and distribution: Impaired seed germination Impaired plant growth |
| Osmotic | Growth on mannitol (in vitro) | Deregulation of ion homeostasis and distribution: Impaired seed germination Impaired plant growth |
| Oxidative | Growth on methyl viologen (in vitro) | ROS formation, protein denaturation, chlorophyll degradation: Bleaching and death |
| Heat | Growth at high temperature (in vitro) | Protein denaturation: Impaired plant growth |
| Cold | Growth at low temperature (in vitro and in vivo) | ROS formation, membrane disruption: Impaired plant growth |

TABLE 1-continued

| Stress | Corresponding treatment | Effect on the plant |
| --- | --- | --- |
| Drought | Water withholding (in vivo) | Cell growth and photosynthesis repression: Impaired plant growth |

As detailed in the introduction, brassinosteroids are found to have a beneficial impact on growth-related characteristics of plants.

The brassinosteroid receptor BRI1 (BRassinosteroid Insensitive 1) is a LRR (leucine rich repeats containing) transmembrane receptor kinase (Cell, 1997, 90, 929-938). It belongs to a small family in *Arabidopsis* comprising: BRI1 (At4g39400); BRL1 (At1g55610), BRL2 (At2g01950) and BRL3 (At3g13380) (Development, 2004, 131, 5341-5351). BRI1 and homologues are not only directly involved in steroid perception (Nature 2005, 433, 167-171), but also bind with high affinity to systemin (pro-systemin homologue from *Arabidopsis*: At2g22940), a peptide hormone involved in systemic signalling of pathogen resistance responses (PNAS, 2002, 99, 9090-9092). Downstream intracellular pathways for plant steroid signalling have been described (Bioassays, 2001, 23, 1028-1036; Trends in Plant Science, 2004, 9, 91-95).

Another family of receptors involved in the brassinosteroid perception is defined by the RKS (Receptor Kinase-like SERK; Development, 1997, 124, 2049-2062) gene products (WO 04/007712). These RKS gene products are also involved in mediating brassinosteroid signalling in plants and appear to form complexes with the BRI1-like receptors (The Plant Cell, 2004, 16, 3216-3229; Cell, 2002, 110, 213-222; Cell, 2002, 110, 203-212). They are also involved in binding extracellular peptide ligands, represented by candidate peptide ligands like the 14 *Arabidopsis* GASA (Gibberelic Acid Stimulated *Arabidopsis*; Plant Mol. Biol., 1995, 27, 743-752) gene products that have been postulated to bind directly to the 14 *Arabidopsis* RKS gene products (WO 04/007712). GASA proteins contain a pocket in their structure that is postulated to be involved in binding brassinosteroids with high affinity. GASA peptide ligands would thereby act as an intermediate between the RKS/BRI-dimers and the brassinosteroid molecule. The dimerisation complex between RKS and other receptors like BRI1 is a dynamic plasma membrane complex, in which different family-members are able to participate as dimerisation partners.

Modulation of activity of these classes of receptor kinases is regulated by both peptide ligands and steroid hormones. Plant brassinosteroids are available in different forms (described in J. Exp. Botany, 1999, 50, 275-282; The Plant Cell, 2002, 597-5110; Plant Physiol., 2003, 131, 287-297). Apart from these, a number of synthetic agonists or antagonists (Trends in Plant Science, 1999, 4, 348-353) can be used to regulate these receptor activities.

In the protein receptor complex described above the ELS proteins (WO 04/007712) are also involved in perception of brassinosteroids and transmission of the signal and thus in mediating the resistance responses throughout the plant. LRP, the tomato homolog of the *Arabidopsis* ELS gene products, is specifically induced and surprisingly also proteolytically processed during pathogenesis (Mol. Gen. Genet., 1994, 243, 47-53; Plant J., 1996, 10, 315-330). ELS protein products are clearly involved in the pathogen resistance responses, and might play a role in the modulation of brassinosteroid regulation of resistance.

Evidence is growing for the convergence of several pathways through which a plant responds to environmental threats. Biotic and abiotic stresses are perceived by intricate mechanisms leading to the regulation of large sets of genes, most of which are specific for a given stress, but common genes are also regulated by several independent stresses (Fujita, M. et al., 2006, Curr. Opin. Plant Biol. 9(4):436-442).

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

A "coding" or "encoding" sequence is the part of a gene that codes for the amino acid sequence of a protein, or for a functional RNA such as a tRNA or rRNA and specifically refers to the fact that the nucleic acid sequence comprises the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein. When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ.

"Expression" refers to the transcription of a gene into structural RNA (rRNA, tRNA) or messenger RNA (mRNA) with subsequent translation into a protein.

The term "sequence identity" as used herein denotes the presence of identity between two or more polynucleotides or between two or more polypeptides. Polynucleotides or polypeptides have "identical" sequences if the sequence of nucleotides respectively amino acids in their sequences is the same when aligned for maximum correspondence. Sequence comparison between two or more polynucleotides or polypeptides is generally performed by comparing portions of two sequences over a comparison window to identify and compare local regions of sequence similarity. The comparison window is generally from about 20 to 200 contiguous nucleotides or from about 7 to 70 contiguous amino acids. The "percentage of sequence identity" for polynucleotides or polypeptides, such as 50, 60, 70, 80, 90, 95, 98, 99 or 100 percent sequence identity may be determined by comparing two optimally aligned sequences over a comparison window, wherein the portion of the polynucleotide or polypeptide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by inspection. Algorithms and software suitable for use in aligning sequences for comparison and calculation of sequence homology or identity will be known to those skilled in the art. Significant examples of such tools are the Pearson and Lipman search based FASTA and BLAST programs, details of these may be found in Altschul et al (1997), Nucleic Acid Res. 25:3389-3402; Altschul et al (1990), J. Mol. Biol. 215: 403-10; Pearson and Lipman (1988), Proc. Natl. Acad. Sci. USA 85:2444-8; Lipman and Pearson (1985), Science 227:1435-41). Other suitable programs include the PILEUP, LINEUP, GAP, BESTFIT and FASTA programs in the GCG® Wisconsin Package® of the University of Wisconsin Genetics Computer Group, Madison, Wis., USA, now offered through Accelrys Inc. Details of the above programs are available on the internet through world wide website www.ncbi.nlm.nih.gov/BLAST or mirror sites and world wide website www.accelrys.com/products/gcg_wisconsin_package. Thus such homology and identity percentages can be ascertained using publicly or commercially available software packages or by computer servers on the internet. By the term "identity" is meant that the stated percentage of the claimed amino acid sequence or nucleic acid sequence is to be found in the reference sequence in the same relative positions when the sequences are optimally aligned, notwithstanding the fact that the sequences may have deletions or additions in certain positions requiring introduction of gaps to allow alignment of the highest percentage of amino acids or bases. Preferably the sequences are aligned by using 10 or less gaps, i.e. the total number of gaps introduced into the two sequences when added together is 10 or less. The length of such gaps is not of particular importance but generally will be no more than 10, and preferably no more than 5 amino acids, or 30 and preferably no more than 15 bases.

The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations". Every nucleic acid sequence herein that encodes a polypeptide also, by reference to the genetic code, describes every possible silent variation of the nucleic acid.

The term "complementary" in "complementary strand" means that the nucleic acid strand has a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

The expression "conservative substitutions" as used with respect to amino acids relates to the substitution of a given amino acid by an amino acid having physicochemical characteristics in the same class. Thus where an amino acid in an RKS sequence has a hydrophobic group, a conservative substitution replaces it by another amino acid also having a hydrophobic group; other such classes are those where the characteristic group is hydrophilic, cationic, anionic or contains a thiol or thioether. Such substitutions are well known to those of ordinary skill in the art, i.e. see U.S. Pat. No. 5,380, 712. Conservative amino acid substitutions may be made, for example within the group of aliphatic non-polar amino acids (Gly, Ala, Pro, Ile, Leu, Val), the group of polar uncharged amino acids (Cys, Ser, Thr, Met, Asn, Gln), the group of polar charged amino acids (Asp, Glu, Lys, Arg) or the group of aromatic amino acids (His, Phe, Tyr, Trp).

The term "selection marker" refers to a polynucleotide sequence encoding a metabolic trait, which allows for the separation of transgenic and non-transgenic organisms and mostly refers to the provision of antibiotic resistance. A selectable marker is for example the NPTII encoded kanamycin resistance marker, the HPT gene, the gene coding for hygromycin resistance. Other selection markers are for instance reporter genes such as chloramphenicol acetyl transferase, β-galactosidase, luciferase and green fluorescence protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates.

As used herein, the term "vector" includes reference to a nucleic acid used in transformation or transfection of a host cell and into which can be inserted a polynucleotide. Vectors are often replicons. Expression vectors permit transcription of a nucleic acid inserted therein.

As used herein, the term "operably linked" refers to a functional linkage or juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell, which contains a vector and supports the replication and/or expression of the vector. Host cells may be prokaryotic cells such as E. coli, or eukaryotic cells such as plant, yeast, insect, amphibian, or mammalian cells. Preferably, host cells are bacterial cells or plant cells, more preferably plant cells.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "regulatory sequence" or "control sequence" is defined herein to include any component, which is necessary or advantageous for expression of a coding sequence. A regulatory sequence may be native or foreign to the coding sequence. Such regulatory sequences include, but are not limited to, a leader, a polyadenylation sequence, a propeptide sequence, a promoter, a signal sequence, and a transcription terminator. At a minimum, the regulatory sequences include a promoter, and transcriptional and translational start and stop signals. The regulatory sequences may be provided with linkers for the purpose of introducing specific restriction sites facilitating ligation of the regulatory sequences with the coding region of the nucleic acid sequence encoding a polypeptide.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. A "plant promoter" is a promoter capable of initiating transcription in plant cells whether or not its origin is a plant cell. Exemplary plant promoters include, but are not limited to, those that are obtained from plants, plant viruses, and bacteria, which comprise genes expressed in plant cells such as Agrobacterium or Rhizobium. Examples of suitable promoters are the 35S promoter of Cauliflower mosaic virus and derivatives thereof, the ferredoxin promoter, the nopaline synthase (nos), mannopine synthase (mas) and octopine synthase (ocs) promoters (EP 0 122 791, EP 0 126 546, EP 0 145 338), the ubiquitin promoter (EP 0 342 926), the cassava vein mosaic virus promoter and the chrysanthemum promoter for the short subunit of Rubisco.

The term "transgenic plant or plant cell" includes reference to a plant or plant cell, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. Also, it is possible that the heterologous polynucleotide is not or not stably integrated in the genome of the transformed plant. In that case, the gene can be 'transiently' expressed, implying that expression occurs for a given time, after which the introduced polynucleotide is lost from the cell. For the purposes of this invention, a transgenic plant or plant cell also includes plants or plant cells, which transiently express the heterologous polypeptide. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "insertion" in the context of introducing a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, the term "plant" includes reference to whole plants, plant organs (e.g., leaves, stems, roots, etc.), seeds and plant cells and progeny of said plants or plant cells. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention is generally as broad as the class of higher plants amenable to transformation techniques, including both monocotyledonous and dicotyledonous plants.

The present invention now relates to introducing a nucleotide construct harboring an RKS gene, preferably from the RKS subgroup II, more specifically RKS1 or RKS or from the RKS subgroup III, more specifically RKS12 for conferring tolerance to abiotic stress in plants. The term tolerance is used throughout the specification in the meaning of the capacity of a plant to endure or become less responsive to abiotic stress. The terms tolerance and resistance to abiotic stress may be used interchangeably.

The different domains of RKS gene products or RKS proteins (see also WO 2004/007712) essentially have the following functions: the first domain of the predicted protein structure at the N-terminal end consists of a signal sequence, involved in targeting the protein towards the plasma membrane. Protein cleavage removes this sequence from the final mature protein product (Jain et al. 1994, J. Biol. Chemistry 269: 16306-16310). The second domain consists of different numbers of leucine zipper motifs, and is likely to be involved in protein-protein dimerisation. The next domain contains a conserved pair of cystein residues, involved in disulphate bridge formation. The next domain consists of 5 (or in the case of RKS3 only 4) leucine rich repeats (LRRs), likely to be involved in ligand binding (Kobe and Deisenhofer 1994, TIBS 19: 415-420). This domain is again bordered by a domain containing a conserved pair of cystein residues involved in disulphate bridge formation often followed by a serine/proline rich region. The next domain displays all the characteristics of a single transmembrane domain. At the predicted cytoplasmic site of protein a domain is situated with unknown function, followed by a domain with serine/threonine kinase activity (Schmidt et al. 1997, Development 124: 2049-2062, WO 01/29240). The kinase domain is followed by a domain with unknown function whereas at the C-terminal end of the protein part of a leucine rich repeat is positioned, probably involved in protein-protein interactions.

The RKS family (Receptor Kinase like SERK) forms the LRRII RLK subfamily as defined by Shiu and Bleeker (2001, PNAS, 98:10763-10768) based on the copy number and structural arrangement of the Leucine-Rich-Repeats (LRRs). It consists of 14 members in *Arabidopsis* for which the corresponding genes were first described in WO 01/29240 (see also WO 2004/007712) and are listed below.

| RKS0 | At1g71830 |
| RKS1 | At1g60800 |
| RKS2 | At5g65240 |
| RKS3 | At5g63710 |
| RKS4 | At2g23950 |
| RKS5 | At5g45780 |
| RKS6 | At5g10290 |
| RKS7 | At5g16000 |
| RKS8 | At1g34210 |
| RKS10 | At4g33430 |
| RKS11 | At4g30520 |
| RKS12 | At2g13800 |
| RKS13 | At2g13790 |
| RKS14 | At3g25560 |

The RKS receptors all contain the 3 characteristic domains of this subfamily: an extracellular domain consisting of 5 LRRs arranged in tandem in a single continuous block, a transmembrane domain and an intracellular kinase domain. The first four LRRs of the extracellular domain are full-length (24 amino acids) whereas LRR5 is truncated and consists of 16 residues only. In RKS3 LRR4 is absent. Intron position and number is conserved except in the extracellular domain of RKS3 and in the kinase domain of RKS2 and RKS6.

Based on the amino acid sequence the family can be further subdivided into 3 groups (see WO 01/29240 and WO 2004/007712) also recently described by Zhang et al. (J. Mol. Evol. (2006) 63: 612-621) when looking at the kinase domain. These subgroups are: group I: RKS 2, 3 and 6; group II: RKS 1, 4, 5, 7, 11 and 14; group III: RKS 0, 8, 10, 12 and 13. Furthermore subgroup III has a common SPP box preceding the transmembrane domain (Schmidt et al. (1997) Dev. 124: 2049-2062) absent from the other subgroups. On the other hand Subgroup II distinguishes itself from the others by for example the presence of the 'PSQ' motif in LRR1 or the 'LQNNxI' motif in LRR2 that are conserved across species.

Also comprised within the definition of an RKS gene is a nucleic acid composed of domains from different RKS genes, or even synthetically made domains homologous with the domains of the above-mentioned RKS genes. In this way, for example, the nucleic acid fragment encoding the transmembrane domain of an RKS gene of subgroup II can be replaced with the nucleic acid fragment encoding a transmembrane domain of subgroup III, including the SPP box. It is also possible that the codon usage of the RKS gene is adapted to the codon usage, which would be optimal for the plant to be transformed.

Plant homologues of the *Arabidopsis* RKS genes can be found by comparison of various plant databases and comprise amongst others:

YI4600|SBRLK1|*Sorghum bicolor*
BF004020|BF004020|EST432518 KV1 *Medicago truncatata*
AW934655|AW934655|EST353547 tomato
AW617954|AW617954|EST314028 *L. pennellii*
AA738544|AA738544|SbRLK2 *Sorghum bicolor*
AA738545|AA738545|SbRLK3 *Sorghum bicolor*
BG595415|BG595415|EST494093 cSTS *Solanum tuberosa*

AI896277|AI896277|EST265720 tomato
BF643238|BF643238|NF002H05EC1F1045
AA738546|AA738546|SbRLK4 *Sorghum bicolor*
BE658174|BE658174|GM700005A20D5 Gm-r1070 *Glycine max*
BF520845|BF520845|EST458318 DSIL *Medicago truncata*
AC069324|AC069324|*Oryza sativa*
AW761055|AW761055|s170d06.y1 Gm-c1027 *Glycine max*
BE352622|BE352622|WHE0425_G11_M21ZS Wheat
BG647340|BG647340|EST508959 HOGA *Medicago truncata*
AY028699|AY028699|*Brassica napus*
AW666082|AW666082|sk31h04.y1 Gm-c1028 *Glycine max*
AA738547|HAA738547|SbRLK5 *Sorghum bicolor*
BG127658|BG127658|EST473220 tomato
L27821|RICPRKI|*Oryza sativa*
BG238468|BG238468|sab51a09.y1 Gm-c1043 *Glycine max*
BG441204|BG441204|GA_Ea0012C15f *Gossypium arbo.*
AW667985|AW667985|GA_Ea0012C15 *Gossypium arbore.*
AW233982|AW233982|sf32g05.y1 Gm-c1028 *Glycine max*
AP003235|AP003235|*Oryza sativa*
BF460294|BF460294|074A05 Mature tuber
AY007545|AY007545|*Brassica napus*
AC087544|AC087544|*Oryza sativa*
AB041503|AB041503|*Populus nigra*

In RKS4 overexpressing plants the At2g14560 gene product, a marker for brassinosteroid induction but not for auxin induction, is upregulated (see FIGS. 9 and 10 of WO 2004/007712). To study the function of RKS4 in detail both gain- and loss-of-function approaches were followed. The RKS4 full-length cDNA was ectopically expressed in *Arabidopsis* Ws-0 plants under the control of the CaMV 35S promoter and we looked for T-DNA insertion lines in the SALK collection (Alonso et al., 2003 available from NASC the European *Arabidopsis* seed-stock centre). The insertion line SALK_066568 renamed rks4-1 was studied along with overexpression lines (RKS4-OX). Changes in RKS4 steady state mRNA level were verified by RT-PCR in 12 d seedlings, which showed that the RKS4 gene is indeed overexpressed in RKS4-OX plants and that its full-length messenger is no longer detectable in rks4-1 plants (data not shown). Nevertheless the 5' end of the RKS4 mRNA (upstream of the T-DNA insertion) is still transcribed in the rks4-1 line and the level of truncated messenger produced was higher than in all other samples. This fragment corresponds to a partial extracellular domain of the RKS4 receptor (first 531 base pairs of the coding sequence). Since the mutant line showed phenotypes similar to that of RKS4-OX plants both at the morphological level and in terms of disease resistance, overexpression constructs corresponding to truncated forms of the RKS4 receptor (RKS4m1-OX (first 531 bp, as in rks4-1) and RKS4m2-OX (first 618 bp, including all LRR domains)) were made and transformed into *Arabidopsis* in order to try mimicking this situation and study its effect in more detail. In this application a truncated RKS gene is defined as an RKS gene comprising at least the first 531 basepairs of the full length RKS gene. Similarly, a truncated RKS protein is defined as a protein encoded by at least the first 531 basepairs of the full length RKS gene.

Figure 1A:
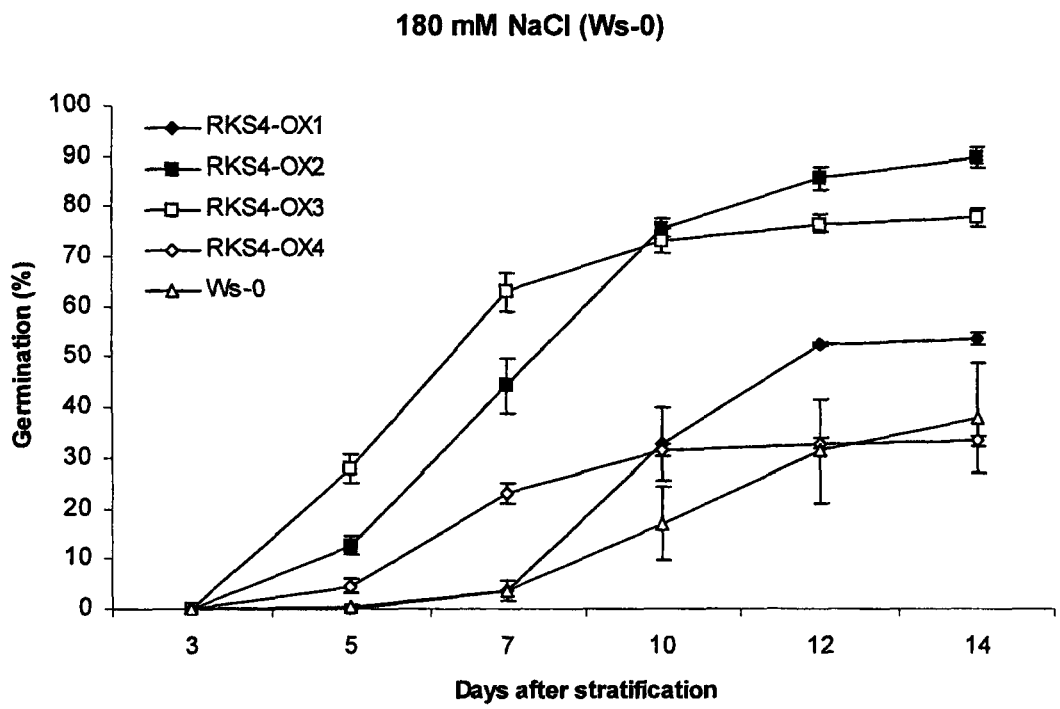
FIG. 1. Effect of high salinity stress on *Arabidopsis* seed germination.
Figure 1B:
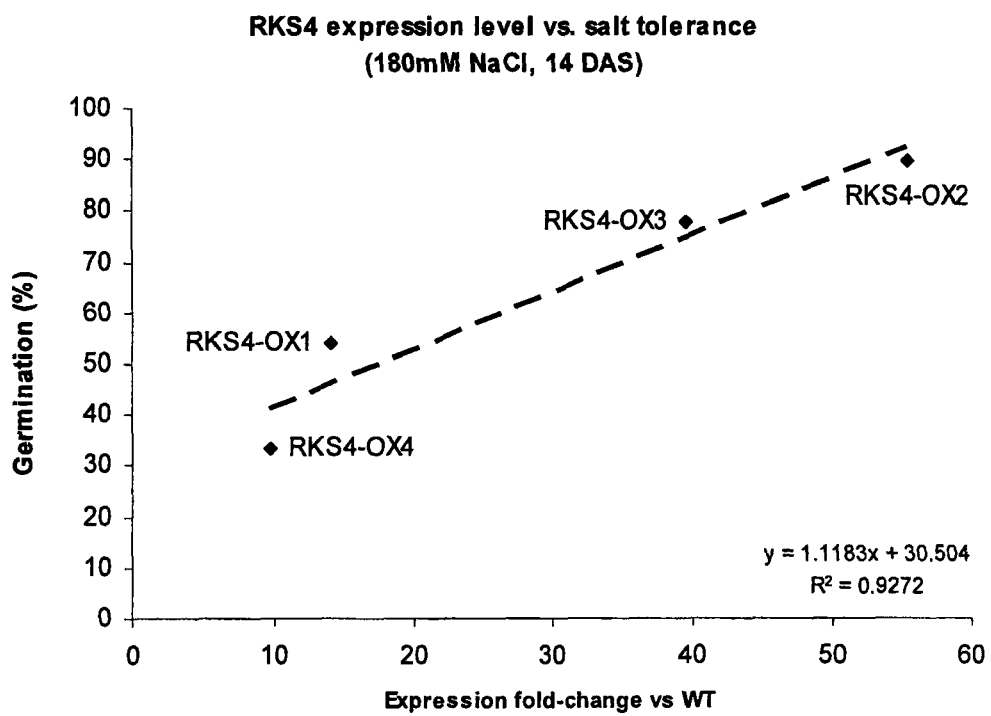
Figure 1C:
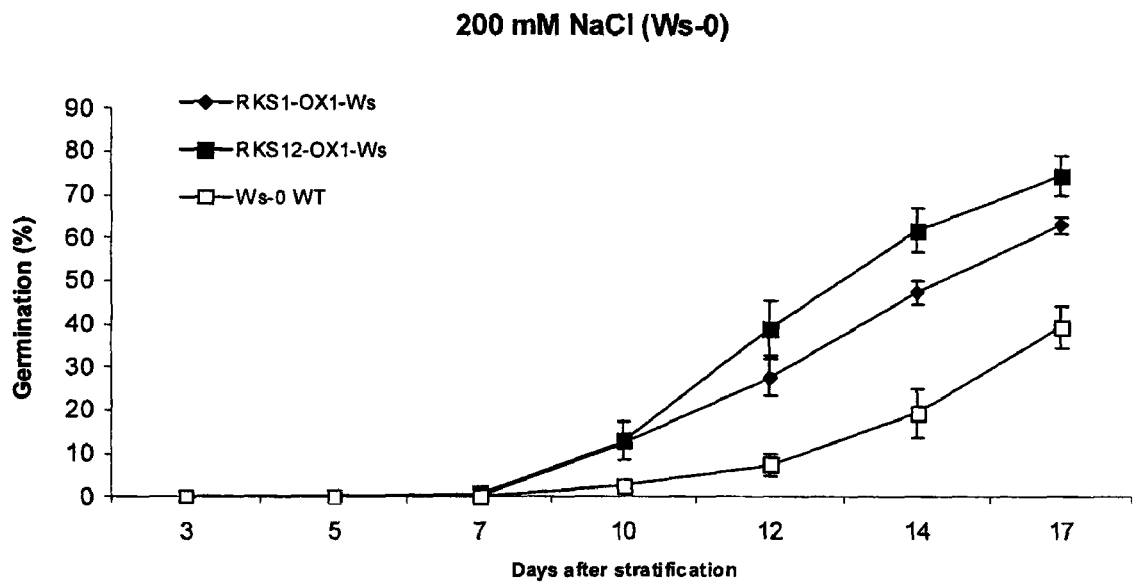
Figure 1D:
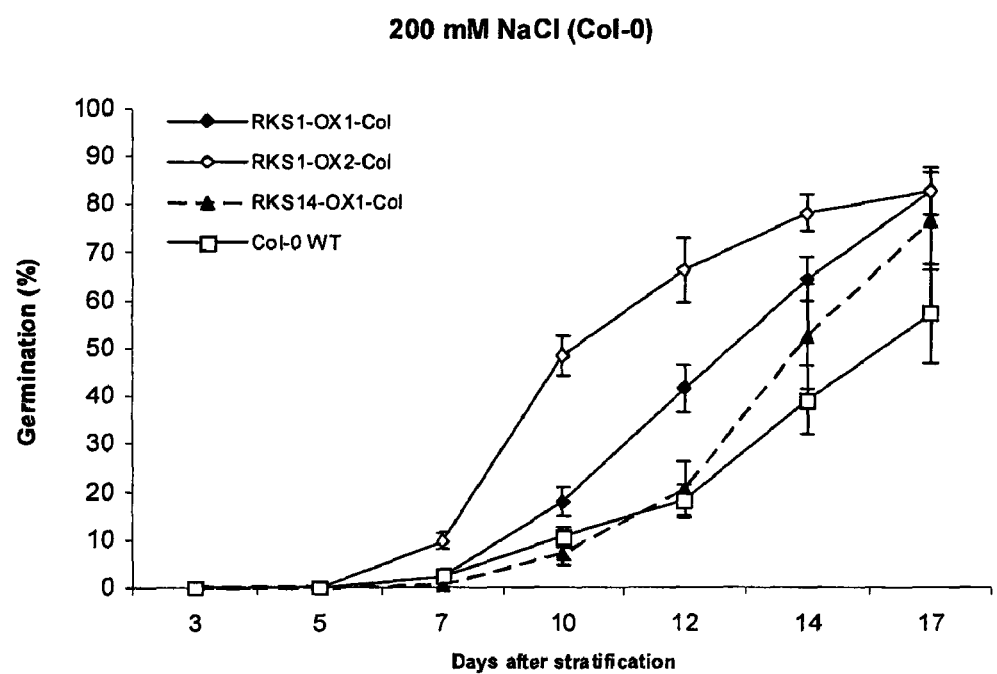

Overexpression of RKS4 appeared to confer tolerance to abiotic stress more specifically in the case of high salt stress (FIG. 1A) and to a lesser extent to osmotic stress (FIG. 2), whereas overexpression of the truncated RKS4 forms gave protection against frost damage as was also observed with rks4-1 plants (FIG. 3). The role of RKS receptors in abiotic stress was further confirmed by overexpression of RKS1, another member of subgroup II and RKS12 a member of subgroup III. Both gave increased tolerance to high salt stress (FIG. 1C).

Based on transcriptome and metabolome analyses of RKS4 transgenic *Arabidopsis* plants we hypothesise that RKS-mediated tolerance to abiotic stress is achieved among others through:

1) the modulation of the GABA shunt metabolic pathway known to be rapidly activated by several abiotic stresses that cause the production of reactive oxygen species (ROS, Bouché and Fromm (2004) TIPS 9: 110-115). The level of γ-amino butyric acid (GABA), for which there is increasing evidence for a role in stress tolerance (Kinnersley and Turano (2000) Crit. Rev. Plant Sci. 19: 479-509), is increased in the RKS4 plants together with that of e.g. glutamate, fumarate, alanine and proline. Increase in these compounds is concomitant with a decrease in gallic acid that inhibits the enzyme glutamate decarboxylase (GAD) converting glutamate into GABA and with a decrease in formic acid that inhibits the conversion of succinate into fumarate within the TCA cycle. Interestingly GAD is actively induced in *E. coli* when exposed to stress and is hypothesized to contribute to cytosolic pH regulation through GABA production (Bouché and Fromm (2004) TIPS 9: 110-115). In turn GABA is also a precursor of alanine, which level is higher in RKS4 plants and glutamate is a precursor of proline, which level is also elevated in the same plants. Increased proline levels are also commonly associated with osmotic and salt stress (Roosen et al. (1998) Plant Phys. 117: 263-271 and Armengaud et al. (2004) Plant Phys. 120: 442-450, respectively).

2) the modulation of the flavonol synthesis pathway and more specifically at the level of quercetin and kaempferol biosynthesis. Apart from their involvement in the prevention of cancer and cardiovascular diseases (Graf et al. (2005) J. Med. Food 8: 281-290) flavonoids in general including flavonols are proposed to also have functions in plants such as UV-protection, defence and resistance against biological and non-biological agents and interaction with plant hormones (Winkel-Shirley (2002) Curr. Opin. Plant Biol. 5: 218-223). In RKS4 transgenic plants elevated levels of various forms of kaempferol are found together with those of quercetin glucoside. Both flavonol derivates have a strong antioxidant potential conferring them the ability to serve as detoxifying agents (Torres et al. (2006) J. Exp. Bot. 57: 1933-1947) and as for GABA play a role in protection against ROS production. In addition a link between GABA and stress-induced phenylpropanoid (including flavonoids) production is proposed via the TCA cycle to which GABA would provide an alternative carbon source in order to allow flavonoid production upon stress (Kinnersley and Turano (2000) Crit. Rev. Plant Sci. 19: 479-509).

3) the modulation of choline biosynthesis which level is increased in RKS4 plants and its use as a precursor for the biosynthesis of for example glycine beatine, which apart from being an osmoprotectant confers tolerance to salinity, drought and other environmental stresses (Mc- Neil et al. (2001) PNAS 98: 10001-10005). Interestingly glycine is also more abundant in RKS4 plants whereas the level of a beatine analogue is decreased. The elevated choline level observed can also be derived from a modulated sinapate ester biosynthesis pathway, through increased hydrolization of sinapine leading to the production of sinapic acid (more abundant in RKS4) and choline (Strack (1981) Z. Naturforsch. 36c: 215-221).

Polynucleotide constructs for expression of a gene such as the RKS gene in the plant nucleus preferably comprise appropriate 3' sequences, such as 3' regulatory sequences or transcription terminators, to be operably linked downstream of the heterologous nucleotide sequence. Several such terminators are available and known in the art (e.g. tm1 from CaMV, PotPI II from potato, E9 from rbcS). Any available terminator known to function in plants can be used in the context of this invention. Numerous other sequences can be incorporated into polynucleotide constructs for expression of a DNA molecule described in this invention. These include sequences, which have been shown to enhance expression such as intron sequences (e.g. from Adh1 and bronze1) and viral leader sequences (e.g. from TMV, MCMV and AMV).

The polynucleotide construct comprises a recombinant polynucleotide for expression of the RKS gene, preferably an RKS gene of subgroup II, more preferably the RKS4 gene. Said gene preferably comprises a nucleic acid which codes for an RKS protein, a homologous RKS protein or a functional fragment thereof. A functional fragment of said protein is defined as a protein which is homologous to the wild-type RKS protein and which remains functional when expressed in a plant, wherein said functionality means that it is capable of conferring resistance to abiotic stress. In this sense also the truncated RKS4 proteins can be considered functional fragments.

Homologous in this sense means that an amino acid sequence has a sequence identity of more than 50%, preferably more than 70%, more preferably more than 80% and most preferably more than 90% with the above mentioned sequence. Alternatively, homology is judged at the nucleotide level, in which homologous means that a nucleotide sequence has sequence identity of more than 50%, preferably more than 70%, more preferably more than 80% and most preferably more than 90% with the wild-type RKS gene or fragment thereof.

The polynucleotide construct of the present invention is preferable constructed such that it comprises at least and in operable linkage a first promoter that is functional in plants, a nucleotide sequence encoding an RKS gene, preferably RKS4, and a terminator. Optionally the polynucleotide may comprise a gene sequence encoding a selectable or screenable marker operably linked to regulatory sequences for expression.

Preferably a viral promoter, such as a promoter from cassava vein mosaic virus (CVMV) or a promoter from cauliflower mosaic virus (CMV) is used. However, any promoter that provides for constitutional expression (such as the 35S or the enhanced 35S promoter) may be used.

The recombinant gene constructs may be inserted into a vector, which may be commercially available, suitable for transforming into plants and suitable for expression of the gene product in the transformed cells. Preferably used are binary vectors (such as pMOG22, known from Goddijn, O. J. M. et al., 1993, Plant J, 4:863-873) which are useful for plant transformation using *Agrobacterium*.

In principle any transformation method may be used to introduce chimeric DNA according to the invention into a suitable ancestor cell. Methods may suitably be selected from the calcium/polyethylene glycol method for protoplasts, electroporation of protoplasts, microinjection into plant material, (DNA or RNA-coated) particle bombardment of various plant material, infection with (non-integrative) viruses, in planta *Agrobacterium tumefaciens* mediated gene transfer by infiltration of adult plants or transformation of mature pollen or microspores (EP 0 301 316) and the like. A preferred method according to the invention comprises *Agrobacterium*-mediated DNA transfer. Especially preferred is the use of the so-called binary vector technology as disclosed in EP 0 120 516 and U.S. Pat. No. 4,940,838.

A method for production of a transgenic plant or plant part according to the invention may comprise the step of selecting transformed plants or plant parts. Generally after transformation, plant cells or cell groupings are selected for the transfer with the polynucleotide construct comprising the DNA-sequence with the genes encoding the various enzymes or blocking mechanisms according to the invention, followed by steps known to the skilled person in which the transformed material is regenerated into a whole plant and evaluating the transformed plant for the overproduction of RKS protein.

Selectable markers, which may be included as a part of the introduced recombinant DNA, are used to select transformed cells (those containing recombinant DNA) over untransformed cells. Examples of suitable markers include genes that provide antibiotic or herbicide resistance. Cells containing the recombinant DNA are capable of surviving in the presence of antibiotic or herbicide concentrations that kill untransformed cells. Examples of selectable marker genes include the bar gene which provides resistance to the herbicide Basta; the nptII gene which confers kanamycin resistance; the hpt gene which confers hygromycin resistance; and the cah gene which gives resistance to cyanamid. An entire plant can be generated from a single transformed plant cell through cell culturing techniques known to those skilled in the art.

A process for obtaining a transgenic plant according to the invention may in an alternative embodiment comprise introducing a vector according to the invention into an ancestor plant, and then producing said transgenic plant from said ancestor plant.

Yet another alternative embodiment for obtaining a transgenic plant according to the invention may comprise introducing a polynucleotide construct according to the invention into a suitable vector for transforming a plant part to produce a transformed plant part, and then regenerating said transgenic plant from said transformed plant part.

Following DNA transfer and regeneration, putatively transformed plants may be evaluated, for instance using Southern analysis, for the presence of the recombinant DNA according to the invention, copy number and/or genomic organization. In addition, or alternatively, expression levels of the newly introduced DNA may be undertaken, using Northern and/or Western analysis, techniques well known to persons having ordinary skill in the art. Further, phenotypic analysis under abiotic stress conditions may reveal plants that have become resistant due to being transgenic for an RKS gene.

It is also submitted that the transgenic plants in which the coding sequence for an RKS gene, preferably RKS4 is inserted, will be made even more resistant to abiotic stress by providing said plants with a brassinosteroid compound, i.e. a compound which is able to activate the brassinosteroid receptor. Such compounds are preferably chosen from the group comprising brassinolide, epibrassinolide, homobrassinolide and analogs. In view of the protective role of brassinosteroids against abiotic stresses and the role of RKS genes in brassinosteroid signaling, it is amenable to propose that by combining modulated expression of an RKS receptor with application of brassinosteroids tolerance to abiotic stress can be further enhanced than by each of the two methods independently.

Application of the brassinosteroid compounds to the plant is done using conventional application methods, e.g. by spraying or by watering.

EXAMPLES

Example 1

Effect of Abiotic Stresses on Seed Germination (High Salinity and Osmotic Stresses)

For all experiments *Arabidopsis* seeds (wild-type and homozygous transgenic lines) of ecotype Wassilewskija (Ws-0) or Columbia (Col-0) were surface-sterilised in 2% bleach+ 0.01% Tween 20, rinsed 5× in sterile water and plated on MS+vitamins (0.8% agar w/v), supplemented or not with 180 or 200 mM NaCl or 400 and 450 mM mannitol. Stratification was performed at 4° C. in the dark for 24 h before transferring the plates to a growth chamber at 20° C. with a 16 h photoperiod (100 umol·m$^{-2}$·s$^{-1}$).

The percentage of germination was determined every 2 days from 3 days after stratification until 14-17 days for each treatment Results:

The effect of high salt on seed germination was followed in time in order to bring forward possible subtle effects of the transgenes and was monitored using different NaCl concentrations. NaCl concentrations were indeed adjusted to the response of the wild-type control seed stocks corresponding to the different transgenic lines. For example the wild-type of RKS1 and RKS12 overexpression lines germinated rather well even on 180 mM NaCl and differences were therefore only visible at 200 mM. On the other hand, 180 mM was sufficient for the RKS4 lines and their wild-type. Higher germination frequencies were observed for RKS4-OX lines (FIG. 1A), although not for all lines, most probably due to expression level differences that correlates rather well with the ability to germinate in the presence of high salt concentration (see FIG. 1B). For example, line OX2 that also shows the highest expression level of the transgene consistently proved to be more tolerant to high salinity during germination. To verify whether this increase in salt tolerance was restricted to RKS4, overexpression lines of two other RKS genes of the same subgroup (II) RKS1 and RKS14 were tested along with an overexpression line of RKS12 belonging to subgroup III of the RKS family. An increase in salt tolerance was also observed with these lines (FIG. 1C) indicating that overexpression of other RKS genes than RKS4 can confer improved tolerance to salt as well. These results are all the more convincing in the case of RKS1 for which lines from both ecotypes could be tested in parallel. Germination in RKS14-OX was not significantly higher than the wild-type control. However we cannot exclude that the expression of RKS14 is too low to confer improved tolerance to salt since only one line could be tested.

The effect of osmotic stress on seed germination was equally monitored in time and using different concentrations of the osmoticum mannitol. As it was the case for NaCl, a high concentration (450 mM) gave the clearest results (FIG. 2). Similarly to what was found with salt the RKS4 overexpression line OX2 showed the highest level of tolerance to the osmoticum, as illustrated by the highest percentage of seed germination on 450 mM mannitol, whereas the lines overexpressing the truncated forms of RKS4 appeared to be more sensitive.

Example 2

Effect of Low Temperature on Plant Growth

For all experiments *Arabidopsis* seeds (wild-type and homozygous transgenic lines) of ecotype Wassilewskija (Ws-0) or Columbia (Col-0) were surface-sterilised in 2% bleach+ 0.01% Tween 20, rinsed 5× in sterile water and plated on MS+vitamins (0.8% agar w/v), supplemented or not with 10 g/l sucrose (=MS10). Stratification was performed at 4° C. in the dark for 24 h before transferring the plates to a growth chamber at 21° C. with a 16 h photoperiod (100 umol·m$^{-2}$·s$^{-1}$). After 10 days, 20 seedlings per sample were transferred to fresh plates containing the same medium. Seedlings were grown further for 10 more days under the same temperature and light conditions, after which all plates were wrapped in aluminium foil and placed for 1 hour at either −25° C. or at room temperature (control plates). Seedlings were subsequently transferred to soil following a randomisation scheme to correct for position effects and the rosette diameter of each plantlet was measured. Plants were then grown on soil at 21° C. with a 16 h photoperiod (100 umol·m$^{-2}$·s$^{-1}$) and their rosette diameter was measured again 7 and 14 days after treatment. A difference in growth reduction as result of the treatment was considered as a criterion for changes in tolerance to freezing damage. Statistical significance was determined by using a student t-test (p-value<0.05).

Figure 3A:
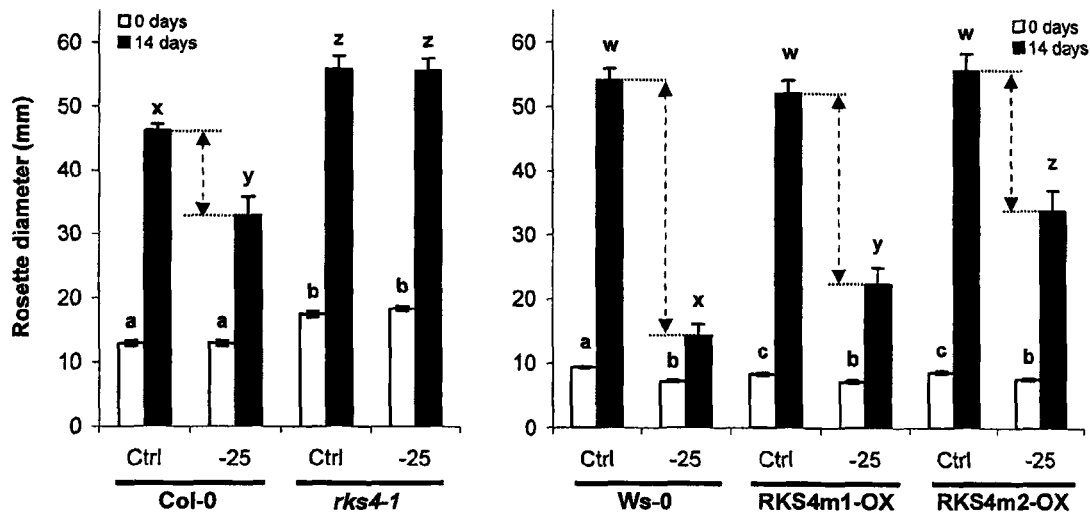
Figure 3B:
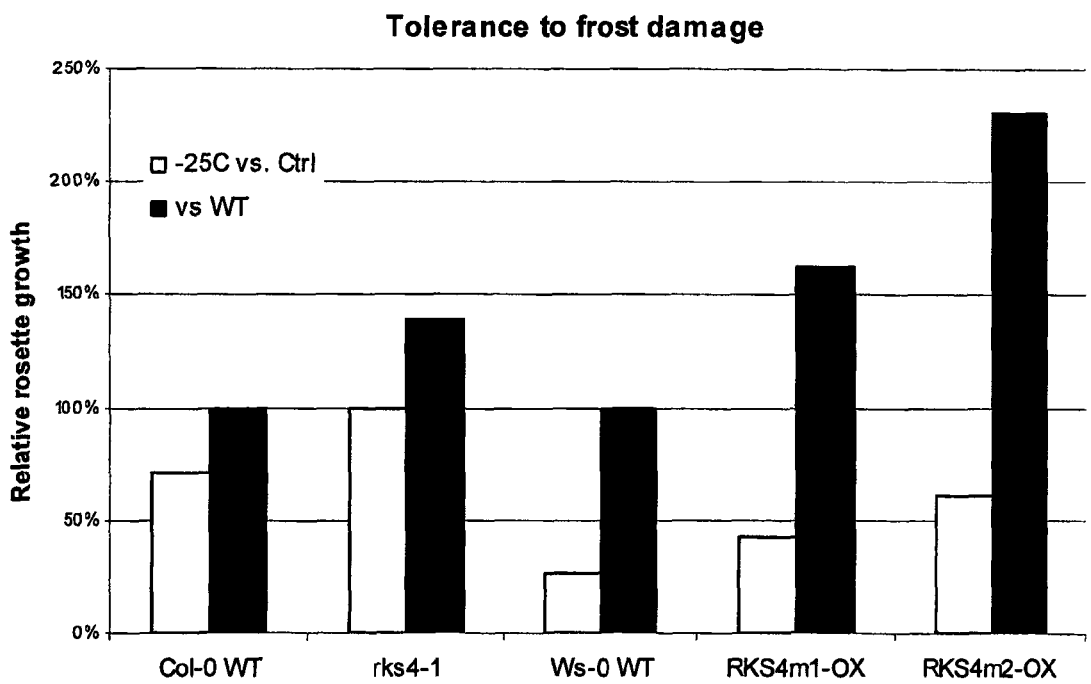

Results:

The frost treatment as applied in our experiments resulted in severe growth inhibition and was measured in terms of rosette diameter. More tolerant plants will suffer less from the treatment and will have a rosette size after treatment that is closer to that of non-treated plants than it is the case with sensitive plants. Our measurements clearly show that rks4-1 plants are more tolerant to freezing damage than the wild-type (Col-0) as their rosette size 14 days after treatment does not differ from that of the control plants (FIG. 3A, left panel). The Col-0 plants however grow slower after treatment as compared to the non-treated control plants. Interestingly, the lines overexpressing truncated forms of the RKS4 gene that are comparable to the partial transcript produced in rks4-1 also show improved tolerance to frost damage (FIG. 3A, right panel). These results also reveal a difference in sensitivity to the treatment between the 2 ecotypes used. The effect is much more severe on Ws-0 than on Col-0 and as such the increase in tolerance for RKS4-m1-OX and RKS4m2-OX seems less important than for rks4-1. Nevertheless if one translates the rosette diameter difference between treated and non-treated plants into relative growth it is clear that the increase in tolerance is substantial in all transgenic lines shown (FIG. 3B). This is especially clear when the differences are related to the wild-type relative growth. The effect of frost damage appears then to be even less important for RKS4-m1-OX and RKS4m2-OX than for rks4-1. They do indeed grow 1.6 and 2.3 times, respectively, better than the wild-type, whereas this is 1.4 times for rks4-1. Therefore by overexpressing a truncated form of the RKS4 gene (extracellular LRRs) improved tolerance to frost damage can be obtained. Based on the effect of the truncated RKS4 receptor it is reasonable to assume that the same result can be achieved through mutagenesis of the coding sequence downstream of the extracellular LRRs.

What is claimed:

1. A method of conferring abiotic stress tolerance to plants by transforming said plants with a nucleotide sequence encoding an RKS gene, subjecting the transformed plant to abiotic stress and selecting transformed plants tolerant to the abiotic stress.

2. The method according to claim 1, wherein said RKS gene is a truncated RKS gene.

3. The method according to claim 1, wherein said RKS gene is RKS1, RKS4, RKS5, RKS7, RKS11, or RKS14.

4. The method according to claim 1, wherein said RKS gene is RKS0, RKS8, RKS10, RKS12 or RKS13.

5. The method according to claim 1, wherein said nucleotide sequence is overexpressed.

6. The method according to claim 1, wherein the plant is additionally treated with a brassinosteroid.

7. The method according to claim 6, wherein said brassinosteroid is brassinolide, epibrassinolide, homobrassinolide or analogs.

8. The method according to claim 1, wherein the abiotic stress is high salinity.

9. The method according to claim 1, wherein the abiotic stress is osmotic stress.

10. The method according to claim 1, wherein the abiotic stress is frost damage.

11. The method according to claim 1, wherein said RKS gene is RKS1 or RKS4.

12. The method according to claim 1, wherein said RKS gene is truncated RKS4.

13. The method according to claim 1, wherein said RKS gene is RKS12.

* * * * *